United States Patent [19]

Chiarino et al.

[11] Patent Number: 4,879,068

[45] Date of Patent: Nov. 7, 1989

[54] PROCESS FOR THE PREPARAITON OF ALKYL FLUORIDES

[76] Inventors: Dario Chiarino, Via Rivolta, 2, 20052 Monza (Milano); Davide Della Bella, Piazza Leonardo da Vinci, 3, 20133 Milano; Giancarlo Jommi, Via Gozzano, 4, 20131 Milano; Domenico Badone, Via Andreoli, 2, 21056 Induno Olona (Varese); Roberto Pagliarin, Via Zara, 29, 20010 San Giorgio su Legnano (Milano); Paolo Tavecchia, Via Volta, 10, 20017 Rho (Milano), all of Italy

[21] Appl. No.: 928,255

[22] PCT Filed: Feb. 12, 1986

[86] PCT No.: PCT/EP86/00086

§ 371 Date: Sep. 30, 1986

§ 102(e) Date: Sep. 30, 1986

[87] PCT Pub. No.: WO86/04893

PCT Pub. Date: Aug. 28, 1986

[30] Foreign Application Priority Data

Feb. 15, 1985 [IT] Italy .................. 19530 A/85

[51] Int. Cl.$^4$ .............. C07C 17/22; C07C 19/02; C07C 71/24; C17J 1/00
[52] U.S. Cl. .................. 260/397; 570/142
[58] Field of Search .......... 570/141, 144, 141; 260/397

[56] References Cited

U.S. PATENT DOCUMENTS

| | | | |
|---|---|---|---|
| 3,080,431 | 3/1963 | Zappel et al. | 570/142 |
| 3,413,321 | 11/1968 | Boswell | 260/397 |
| 4,263,214 | 4/1981 | DeLuca et al. | 260/397.2 |
| 4,594,467 | 6/1986 | Henneke et al. | 570/193 |
| 4,633,026 | 12/1986 | Kolich | 570/193 |

FOREIGN PATENT DOCUMENTS

| | | | |
|---|---|---|---|
| 274464 | 9/1961 | Australia | 570/142 |
| 605473 | 9/1978 | Switzerland | 570/142 |

*Primary Examiner*—J. E. Evans
*Attorney, Agent, or Firm*—Stevens, Davis, Miller & Mosher

[57] ABSTRACT

Preparation of alkyl fluoride by replacement of an aliphatic hydroxy group with fluorine. The reaction is performed by treating a sulfonyl derivative of an aliphatic hydroxy group with an inorganic fluoride in a polyglycol.

5 Claims, No Drawings

PROCESS FOR THE PREPARAITON OF ALKYL FLUORIDES

DESCRIPTION

This invention relates to a process for the preparation of alkyl fluorides by replacing an aliphatic hydroxy group with fluorine.

More particularly this invention relates to the reaction of a sulfonyl derivative of an aliphatic hydroxy group with an inorganic fluoride in a polyglycol.

The sulfonyl derivatives of this invention have the following general formula:

$$R-O-SO_2-R' \qquad (I)$$

wherein
R is alkyl, arylalkyl or cycloalkyl; and
R' is lower alkyl, or aryl.

Although in formula I it is represented a single substituted hydroxy group the number of substituted aliphatic hydroxy groups on the R radical may be higher.

The aliphatic hydroxy group in formula I is primary or secondary in nature.

Typical examples of R' are those radicals known to form, together with $-O-SO_2-$, a leaving group.

Preferred examples of R' are methyl, phenyl, 4-methylphenyl, 2,4,6-trimethylphenyl, 2-naphthyl, and 2-pyridyl.

Typical examples of R are: straight and branched alkyl having from 1 to 22 C atoms, phenyl- and naphthyl-alkyl where the alkyl radical has 1-6 C atoms, cycloalkyl having 3-6 C atoms optionally comprised in a polycyclic system whose skeleton, hence substituents excluded, has up to 22 C atoms. In addition the alkyl, the aryl and the cycloalkyl moiety may in turn be substituted by other groups provided they are inert under the conditions of the process of this invention. Typical examples of such groups are the nitro, ether, thioether, hydroxy, ketone, aldehyde, ketal, thioketal, ester, acylamino and the heterocyclic group.

Examples of polycyclic systems are the compounds containing the following skeleton:

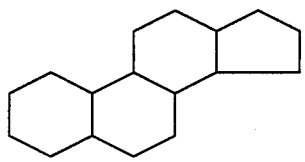

such as cholestane, coprostane, androstane and variously functionalized and/or unsaturated cholane.

Examples of alkyl fluorides which can be prepared according to this invention comprise 3-fluoro-D-alanine (J. Kollonitsch et al., J. Am. Chem. Soc. 98, 5591, 1976; Dolling et al., J.O.C. 43, 1634, 1978), alfa-fluoromethyl-Dopa (M. J. Jung et al., Life Sci. 24, 1037, 1979; A. L. Maycock et al., Biochemistry 19, 709, 1980), alfa-fluromethylglutamic acid (U.S. Pat. No. 4,004,996; D. Kno et al. Biochemistry 20, 506, 1981), 4-fluoromethyl-GABA (E.P. Appln. 0000036) alfa-fluoromethylamino acids (J. Kollonitsch et al., J.O.C. 40, 3808, 1975; J.O.C. 44, 771, 1979). The person skilled in the art will appreciate that when preparing these compounds the amino and the carboxylic groups must be properly protected according to usual techniques.

Other alkyl fluorides which can be prepared in accordance with this invention are some fluoro-derivatives of methaqualone (J. Tani et al., J. Med. Chem. 22, 95, 1979) and 4-fluoromethyl monobactam analogs (E.P. Appln 0114128; J. S. Skotnick et al. J. Antibiot. 36 (9) 1201, 1983).

Furthermore the process fo this invention allows to prepare some intermediate compounds such as 1-fluoro-2-bromo(or chloro)ethane, and 1-fluoro-2-amino-ethane hydrochloride which are useful in the preparation of 6,8-difluoro-1-(2-fluoroethyl)-1,4-dihydro-7-(4-methyl-1-piperazinyl)-4-oxo-3-quinolinecarboxylic acid (Belgian Pat. No. 887,574) and N'-((1alfa, 2beta, 6alfa)-2,6-dihydroxycyclohexyl)-N-(2-fluoroethyl)-N-nitrosourea (T. P. Johnston et al., J. Med. Chem. 27(11), 1422, 1984), respectively.

Known fluorination agents show a number of drawbacks such as expensiveness, toxicity, explosiveness, perishability, and corrosiveness. Examples of such agents are sulfur tetrafluoride (Ang. Chem. Int. Ed. Engl. I, 467, 1962) which is expensive and toxic; diethylaminosulfotrifluoride or DAST (J.O.C. 40, 574, 1975) which is expensive and toxic and whose preparation is dangerous because explosions can occur; the fluoro(phenyl)phosphoranes (Th. Lett 4507, 1978) which are difficult to prepare, toxic, and usually promote the formation of various byproducts; 1-diethylamino-1,1-difluoro-2-chloro-2-fluoro-ethane or FAR (J.C.S. Perkin I 512, 1977; J.C. Res. (S) 46, 1980) which deteriorates easily, is expensive, requires anhydrous conditions, and can only be used with substrates which are fairly soluble in organic, aprotic and low polar solvents; and the hydrofluoric acid/pyridine system (Synthesis, 472, 1973) which exhibits all the dangers of gaseous hydrofluoric acid such as corrosiveness and which often promotes the formation of large quantities of byproducts.

Also known are some fluorination methods which involve the use of fluorides but these, too, have a number of drawbacks.

Thus the use of fluorides supported on polymers (Synthesis, 472, 1976) requires anhydrous conditions both of the solvent and of the resins. In turn, potassium fluoride/crown ethers and dipolar aprotic solvents system (J.A.C.S. 96, 2250, 1974) is toxic while the phase transfer method with potassium fluoride and "onium" catalysts system (Synthesis, 428, 1974) gives rise to often large quantities of hydrolysation and elimination byproducts since the flouride onion behaves also like a strong base.

The process of this invention is preferably carried out by reacting 1 mol of a sulfonyl derivative of an aliphatic hydroxy group with from 1 to 10 mol of an inorganic fluoride in a polyglycol at a temperature of between 40° and 110° C. for from 2 to 170 hours.

Suitable inorganic fluorides are those which give rise to a nucleophilic reaction such as for example the fluorides of alkali and alkaline-earth metals, of ammonium and of phosphonium. Preferred fluorides are sodium and potassium fluoride.

Preferably for each mol of sulfonyl derivative it is added from 3 to 7 mol of inorganic fluoride. The still more preferred amount is 5 mol.

The polyglycols are required to have a viscosity degree (at room temperature and at high temperatures) consistent with the types of treatment to which is submitted the reaction mixture and have the formula $HO-(AO)_n-H$, wherein A is a straight or branched alkylene having 2–6 C atoms and n is an integer number ranging between 4 and 50.

Preferably are used polyethylene glycols having a molar weight of between 200 and 2000. Still more preferably is used polyethylene glycol 400.

The ratio of sulfonyl derivative to polyglycol is approximately 5–10 ml of polyglycol for each gram of sulfonyl derivative.

In the case of polyethylene glycol 400 it is preferred to use 5 ml for each gram of sulfonyl derivative.

To the reaction mixture may be added other organic diluents. This technique is preferred when the sulfonyl derivative is sparingly soluble in the polyglycol. In selecting this diluent it is preferred to avoid the use of those protic solvents which under the reaction conditions may promote the solvolysis of the sulfonyl derivative. Good results are obtained using diethyleneglycoldimethylether.

As to the reaction temperature, it is preferred to work between approximately 50° C. and 70° C.

The following examples illustrate the invention without however limiting it.

EXAMPLE 1

1-phenyl-2-fluoroethane (A) A mixture of phenethyl p-toluenesulfonate (2.317 g, 8.4 mol) and potassium fluoride (2.47 g, 42.6 mol) in 23 ml of polyethylene glycol (PEG) 400 was stirred continuously at 50°14 55° C. for 43 hours.

The mixture was then poured into brine (230 ml) and extracted three times with ethyl ether (3×70 ml).

The combined ethereal extracts were dried over sodium sulfate, filtered on a small silica column dia. 2 cm, height 3 cm), and concentrated at atomospheric pressure with rectification.

824 mg of crude product were thus obtained.

A sample of crude product was tested by GLC using an OV1 column programmed for 2′ at 40° C., then 20° C. per minute up to 180° C., and finally 16′ at 180° C.

The titre of the desired compound was 94.41%.

(B) A mixture of phenethyl p-toluenesulfonate (4.89 g, 24.45 mmol) and potassium fluoride (7.09 g, 122.25 mmol) in 49 ml of PEG 400 was stirred continuously at 50°–55° C. for one week.

The reaction mixture was then treated as described in Example A above and gave 1.884 g of a crude product containing 91.76% of the desired compound.

(C) A mixture of phenethyl methanesulfonate (935 mg, 3.07 mmol) and potassium fluoride (891 mg, 15.3 mmol) in 9.3 ml of PEG 400 was stirred continuously at 60°–65° C. for three days.

The reaction mixture was then treated as described in Example A above and gave 293 mg of a crude product containing 86.10% of the desired compound.

(D) A mixture of phenethyl 2-naphthyl sulfonate (1.009 g, 3.23 mmol) and potassium fluoride (983 mg, 16.16 mmol) in 10.0 ml of PEG 400 was stirred continuously at 55°–76° C. for 40 hours.

The reaction mixture was then treated as described in Example A above and gave 315 mg of a crude product containing 89.1% of the desired compound.

EXAMPLE 2

1-fluoro-octane (A) A mixture of 1-octyl methanesulfonate (5.32 g, 25.5 mmol) and potassium fluoride in 53 ml of PEG 400 was stirred continuously at 50°–55° C. for 50 hours.

The reaction mixture was then treated as described in Example 1A above and gave 1.159 g of a crude product containing 96.17% of the desired product.

(B) A mixture of 1-octyl p-toluenesulfonate (1.45 g, 4.9 mmol) and potassium fluoride (1.43 g, 24.65 mmol) in 14 ml of PEG 400 was stirred continuously at 50°–55° C. for 27 hours.

The reaction mixture was then treated as described in Example 1A above and gave 396 mg of a crude product containing 87.1% of the desired compound.

EXAMPLE 3

2-fluoro-octane (A) A mixture of 2-octyl methanesulfonate (2.384 g, 11.44 mmol) and potassium fluoride (3.32 g, 57.2 mmol) in 23 ml of PEG 400 was stirred continuously at 50°–55° C. for 48 hours.

The reaction mixture was then treated as described in Example 1A above and gave 860 mg of a crude product containing 78.30% of the desired compound.

(B) A mixture of 2-octyl p-toluenesulfonate (2.184 g, 7.7 mmol) and potassium fluoride (2.23 g, 38.4 mmol) in 22 ml of PEG 400 was stirred continuously at 50°–55° C. for 18 hours.

The reaction mixture was then treated as described in Example 1A above and gave 685 mg of a crude product containing 74.81% of the desired compound.

EXAMPLE 4

3alfa-fluoro-cholestane

A mixture of 3beta-cholestane mesylate (648 mg, 2 mmol) and potassium fluoride (580 mg, 10 mmol) in 6.5 ml of PEG 400 and 1.5 ml of chloroform was stirred continously at 105° C. for 30 hours.

The reaction mixture was then treated as described in Example 1A above and gave 32 mg of the desired compound.

EXAMPLE 5

3beta-fluoro-17-ethylenedithioandrostane (A) A mixture of 3alfa-17-ethylendithioandrostane tosylate (304 mg, 0.58 mmol) and potassium fluoride (170 mg, 2.9 mmol) in 3 ml of PEG 400 and 3 ml of diethyleneglycoldimethylether was stirred continuously at 55°–60° C. for 8 days.

The reaction mixture was treated as described in Example 1A above and gave 53 mg of the desired compound.

(B) A mixture of 3alfa-17-ethylenedithioandrostane tosylate (410 mg, 0.787 mmol) and potassium fluoride (228 mg, 3.95 mmol) in 4 ml of PEG 400 and 4 ml of dimethylformamide was stirred continuously at 55°–60° C. for 8 days.

The reaction mixture was then treated as described in Example 1A above and gave 214 mg of a crude product containing 15.78% of the desired compound.

We claim:

1. A process for the preparation of an alkyl fluoride, RF, wherein a sulfonyl derivative of the formula $$R-O-SO_2-R' \qquad (I)$$

wherein R is alkyl, arylalkyl or cycloalkyl and R′ is lower alkyl, or aryl, is reacted at 40° to 110° C. with a sodium, potassium, ammonium or phosphonium fluoride in a polyglycol of the formula $$HO-(AO)_n-H$$

wherein A is a straight or branched alkylene having 2-6 carbon atoms and n is an integer ranging from 4 to 50.

2. A process according to claim 1, wherein a polyethylene glycol having a molecular weight ranging from 200 to 2000 is used.

3. A process according to claim 2, wherein polyethylene glycol 400 is used.

4. A process according to claim 1, wherein an aprotic organic diluent is added to the reaction mixture.

5. A process according to claim 4, wherein the aprotic organic diluent is diethyleneglycol-dimethylether.

* * * * *